United States Patent
Suzuki

(10) Patent No.: US 7,316,703 B2
(45) Date of Patent: Jan. 8, 2008

(54) FORCEPS FOR ENDOSCOPE

(75) Inventor: Keita Suzuki, Tokyo (JP)

(73) Assignee: Olympus Corporation, Tokyo (JP)

( * ) Notice: Subject to any disclaimer, the term of this patent is extended or adjusted under 35 U.S.C. 154(b) by 764 days.

(21) Appl. No.: 10/855,153

(22) Filed: May 27, 2004

(65) Prior Publication Data

US 2005/0033358 A1   Feb. 10, 2005

(30) Foreign Application Priority Data

May 29, 2003   (JP)   ............................. 2003-152606

(51) Int. Cl.
  *A61B 17/28*   (2006.01)
(52) U.S. Cl. ..................................... 606/208
(58) Field of Classification Search ................ 606/170, 606/171, 174, 178, 205–211
  See application file for complete search history.

(56) References Cited

U.S. PATENT DOCUMENTS

| 5,423,854 | A | | 6/1995 | Martin et al. |
| 5,474,571 | A | * | 12/1995 | Lang .......................... 606/205 |
| 5,746,740 | A | | 5/1998 | Nicholas |
| 2002/0055758 | A1 | | 5/2002 | Sasaki |

FOREIGN PATENT DOCUMENTS

| FR | 2681775 | 4/1993 |
| JP | 6-285078 | 10/1994 |
| JP | 2001-299768 | 10/2001 |

* cited by examiner

Primary Examiner—Kevin T. Truong
(74) Attorney, Agent, or Firm—Scully, Scott, Murphy & Presser, P.C.

(57) ABSTRACT

This invention reduces the amount by which members protrude to the outside of a forceps for endoscope that can perform an oscillating operation, and reduces the amount of contact between an organism and parts other than the surgical instruments, thereby maintaining the visual field of the endoscope. The forceps for endoscope comprises an insertion section that is inserted inside a body cavity, an openable and closable forceps section provided at the tip of the insertion section, and a operation section for controlling the forceps section. The forceps section comprises a first forceps member, and a second forceps member, which faces the first forceps member and can rotate with a first pivotal supporting member as a fulcrum; the second pivotal supporting member supports the first forceps member from vertically above it so that it can rotated freely around an oscillating operation axis member, and is provided between the oscillating operation axis member and an opening-closing operation axis member. A third pivotal supporting member supports the first forceps member from vertically outside, so that it can rotate around the oscillating operation axis member.

2 Claims, 4 Drawing Sheets

FORCEPS FOR ENDOSCOPE

BACKGROUND OF THE INVENTION

1. Field of the Invention

This invention relates to a forceps for endoscope used when grasping and severing a living organism.

This application is based on Japanese Patent Application No. 2003-152606, the contents of which are incorporated herein by reference.

2. Description of the Related Art

In surgical treatment performed by inserting a surgical instrument into human abdominal cavities, the abdominal cavities are minimized so as to reduce the burden on the patient; consequently, the treatment must be performed by inserting the surgical instruments into cavities of limited numbers and sizes. To accomplish this, after inserting the surgical instrument into an abdominal cavity, the surgeon uses a forceps for endoscope, which enables him to perform multi-free operations via a one-directional operation (e.g. see Japanese Patent Application, First Publication No. 2001-299768 (FIG. 3)).

According to the multi-free forceps of the above Patent Document, connecting pins and supporting pivots for supporting a connecting member are arranged around the central axis of drive rods, which deviate from their central axis in order to avoid the connecting pins and the supporting pivots. This makes it possible to perform an oscillating operation by assembling a link device, which is connected to operation axis members comprising a plurality of operating rods, change the direction of the device section by a rotating the handle while the multi-free forceps is inserted, thereby grasping the organism, stitch up the organism, and the like.

There has been proposed a forceps for endoscope in which a cam groove or the like is provided at the tip of the operation axis member, and a projection or rod member that is provided on the forceps member slides into the cam groove, reducing the amount of outward protrusion of the insertion section of the forceps (e.g. see Japanese Patent Application, First Publication No. 6-285078 (FIG. 1) and U.S. Pat. No. 5,746,740 (FIG. 4, FIG. 7)).

SUMMARY OF THE INVENTION

The forceps for endoscope of this invention comprises an openable and closable forceps section, provided at the tip of an insertion section; the insertion section having an oscillating operation axis member and a opening-closing operation axis member, which can move forward and backward in the axial direction; the forceps section having a first forceps member and a second forceps member, the second forceps member being rotatable with a first pivotal support as a fulcrum and facing the first forceps member; the first forceps member connecting to the insertion section so as to be rotatable around it with a second pivotal support as a fulcrum, and connecting to the oscillating operation axis member so as to be rotatable around it with a third pivotal support as a fulcrum; the second pivotal support being arranged between the oscillating operation axis member and the opening-closing operation axis member; the first pivotal support being arranged nearer the opening-closing operation axis member side than the second pivotal support; a tip of the opening-closing operation axis member being provided nearer the tip side of the first forceps member than the second pivotal support; and the pivotal supports being arranged from a tip side of the first forceps member to a base side thereof in a sequence of first pivotal support, second pivotal support, third pivotal support.

The forceps for endoscope of this invention comprises a connecting member for connecting the second forceps member to the opening-closing operation axis member; one end of the connecting section being connected to the opening-closing operation axis member so that it can rotate around it with a rotation axis member as a fulcrum; another end of the connecting section being connected to a base of the second forceps member so that it can rotate around it with a fourth pivotal support as a fulcrum; the fourth pivotal support being arranged on the opposite side of the rotation axis member with respect to the central axis of the forceps section; the first forceps member having a leading groove, which the rotation axis member clips into; and the leading groove extending from the base side of the first forceps member toward the tip side thereof, and diagonally from the opening-closing operation axis member side toward the fourth pivotal support side.

DESCRIPTION OF THE PREFERRED EMBODIMENT

A preferred embodiment of the invention will be explained with reference to FIG. 1 to 4.

Figure 1:
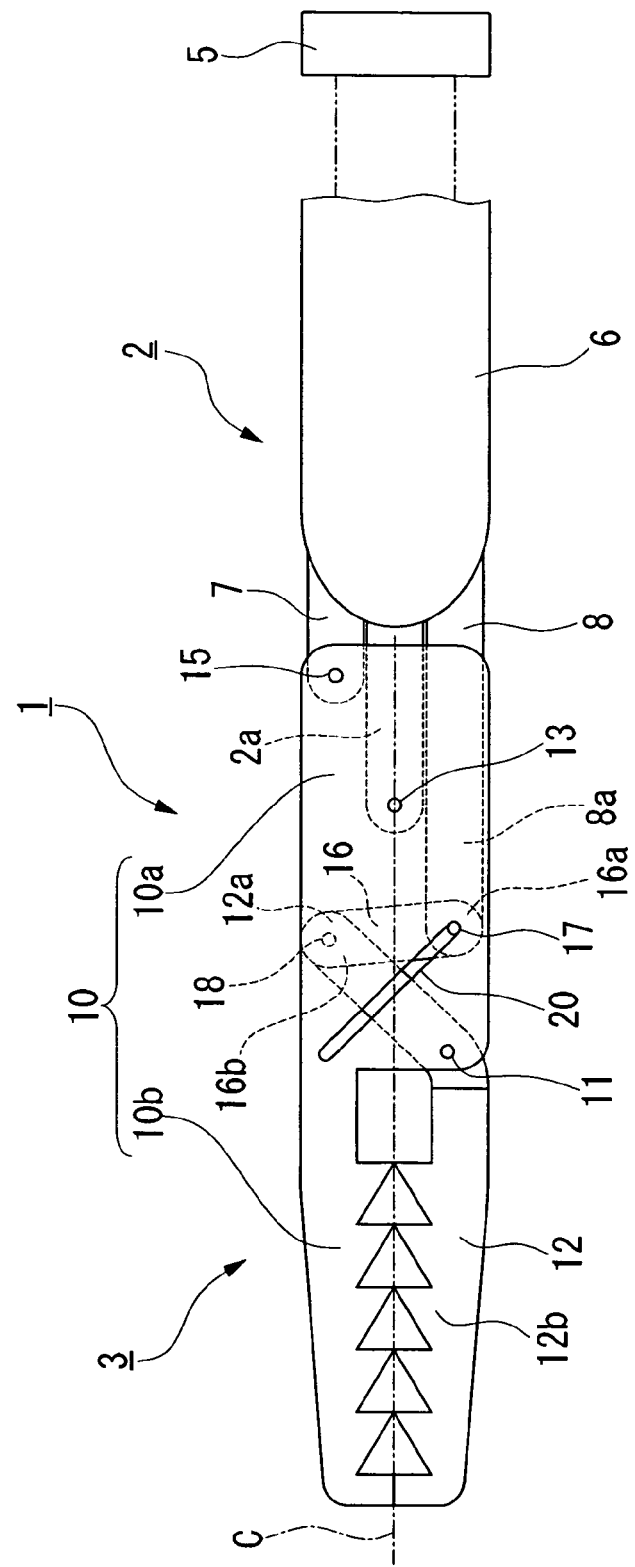
FIG. 1 is a cross-sectional view of primary parts of a forceps for endoscope according to an embodiment of this invention.

As shown in FIG. 1, a forceps for endoscope 1 according to this embodiment comprises an insertion section 2 that is inserted into a body cavity, an openable and closeable forceps section 3, provided at a tip section 2a of the insertion section 2, and an operation section 5 for operating the forceps section 3.

The insertion section 2 is fitted with a tubular seizing member 6 having flexibility around its outer peripheral face, an oscillating operation axis member 7, which can move forward and backward in the axial direction, and an opening-closing operation axis member 8, which can move forward and backward in the axial direction together with the oscillating operation axis member 7, being provided inside the seizing member 6.

The operation section 5 connects to the insertion section 2, and operates the forceps section 3 by moving the oscillating operation axis member 7 and the opening-closing operation axis member 8 backward and forward in their respective axial directions.

The forceps section 3 comprises a first forceps member 10 and a second forceps member 12, which faces the first forceps member 10 and can rotate with a first pivotal supporting member (first pivotal support) 11 as its fulcrum.

The first forceps member 10 is formed from an approximately rod-shaped metal piece, and is connected to the tip section 2a of the insertion section 2, which it can rotate around with a second pivotal supporting member (second pivotal support) 13 at the base 10*a* side as its fulcrum; in addition, the first forceps member 10 is connected to the oscillating operation axis member 7, which it can rotate around with a third pivotal supporting member (third pivotal support) 15 as its fulcrum.

As shown in FIG. 1, the forceps section 3 has a connecting member 16, which connects the second forceps member 12 to the opening-closing operation axis member 8. One end 16*a* of the connecting member 16 is connected to the opening-closing operation axis member 8, which it can rotate around with a rotating axis member 17 as its fulcrum, and another end 16*b* of the connecting member 16 is connected to the base 12*a* of the second forceps member 12, which it can rotate around with a fourth pivotal supporting member 18 as its fulcrum. The fourth pivotal supporting member (fourth pivotal support) 18 is provided on the opposite side of the rotating axis member 17 with respect to the central axis C of the forceps section 3.

The tip 8*a* of the opening-closing operation axis member 8, which connects to the connecting member 16, is bendable so that it can follow the movement of the rotating axis member 17.

The first forceps member 10 is fitted with a leading groove 20, which has a predetermined width and clips to the rotating axis member 17; the leading groove 20 runs from the base 10*a* side of the first forceps member 10 toward the tip 10*b* side, and extends in a straight line diagonally from the opening-closing operation axis member 8 side toward the fourth pivotal supporting member 18 side.

The contacting faces of the rotating axis member 17 and the leading groove 20 may be coated so that they slide easily.

The tip 12*b* of the second forceps member 12 extends in opposition to the tip 10*b* of the first forceps member 10. It then bends from the position of the first pivotal supporting member 11 toward the oscillating operation axis member 7 side, and connects to the other end 16*b* of the connecting member 16 at the base 12*a* via the fourth pivotal supporting member 18.

The second pivotal supporting member 13 supports the first forceps member 10 from vertically above it so that it can rotated freely around the oscillating operation axis member 7, and is provided between the oscillating operation axis member 7 and the opening-closing operation axis member 8.

As shown in FIG. 1, the first pivotal supporting member 11 is the base point when opening and closing the first forceps member 10 and the second forceps member 12, and is provided nearer to the opening-closing operation axis member 8 side than the second pivotal supporting member 13.

The tip 8*a* of the opening-closing operation axis member 8 is provided nearer to the tip 10*b* of the first forceps member 10 than the second pivotal supporting member 13.

The first pivotal supporting member 11 and the third pivotal supporting member 15 are arranged separately on opposite sides of the central axis C of the forceps section 3; in addition, the first pivotal supporting member 11, the insertion section 2, and the third pivotal supporting member 15, are arranged in this sequence from the tip 10*b* of the first forceps member 10 to the base 10*a*.

Subsequently, the method for using the forceps for endoscope 1 according to the embodiment described above will be explained.

Figure 2:
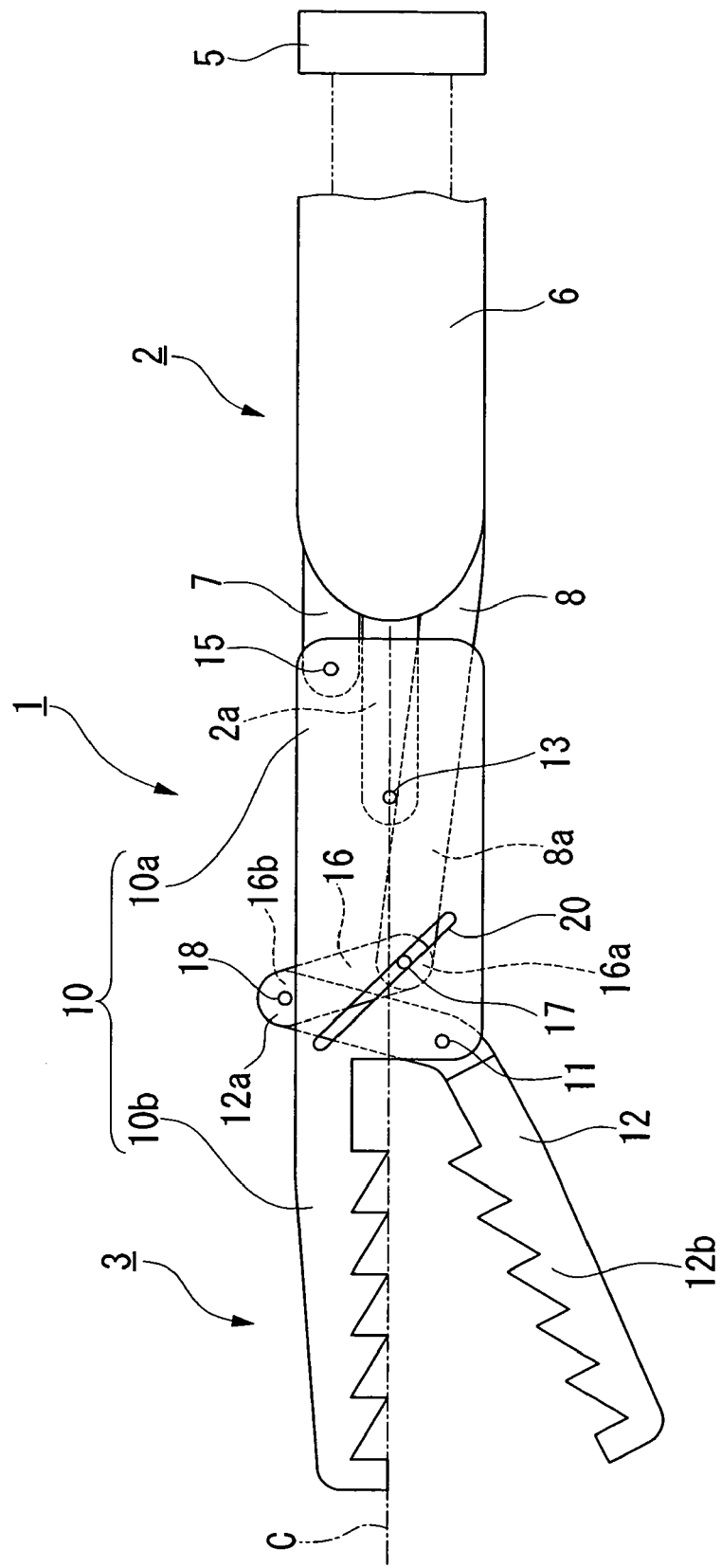
FIG. 2 is a side view of primary parts of the forceps for endoscope according to the embodiment of this invention in an open state.

Firstly, a method of switching from a state where the first forceps member 10 and the second forceps member 12 are closed, as shown in FIG. 1, to a state where the second forceps member 12 is open, as shown in FIG. 2, will be explained.

In the state shown in FIG. 1, the operation section 5 is manipulated to move the opening-closing operation axis member 8 forward to the forceps section 3 side. At this time, a force acts on the rotating axis member 17 provided at the tip of the opening-closing operation axis member 8, turning it toward tip of the forceps for endoscope 1, but a resistive force from the leading groove 20 guides it in the direction of the leading groove 20.

When the opening-closing operation axis member 8 is moved further forward, the rotating axis member 17 moves along the leading groove 20 toward the tip 10*b* side of the first forceps member 10; this pushes the fourth pivotal supporting member 18 outside the first forceps member 10, and, via the fourth pivotal supporting member 18, pushes the base 12*a* of the second forceps member 12 outside. Then, the tip 12*b* side of the second forceps member 12 rotates counterclockwise (as seen in FIG. 1) around the first pivotal supporting member 11.

Next, as shown in FIG. 2, the second forceps member 12 rotates downward with respect to the first forceps member 10 so that both reach an open state.

When closing the second forceps member 12 so that it once more is positioned opposite the first forceps member 10, the operation section 5 is manipulated so as to move the opening-closing operation axis member 8 backward to the operation section 5 side.

Since the rotating axis member 17 is now guided by the leading groove 20 toward the opening-closing operation axis member 8 side, and pulled back to the base 10*a* side of the first forceps member 10, the base 12*a* of the second forceps member 12 moves toward the inner side of the first forceps member 10 via the fourth pivotal supporting member 18, and the second forceps member 12 rotates clockwise (as seen in FIG. 2) around the first pivotal supporting member 11. In this way, the first forceps member 10 and the second forceps member 12 are closed.

Figure 3:
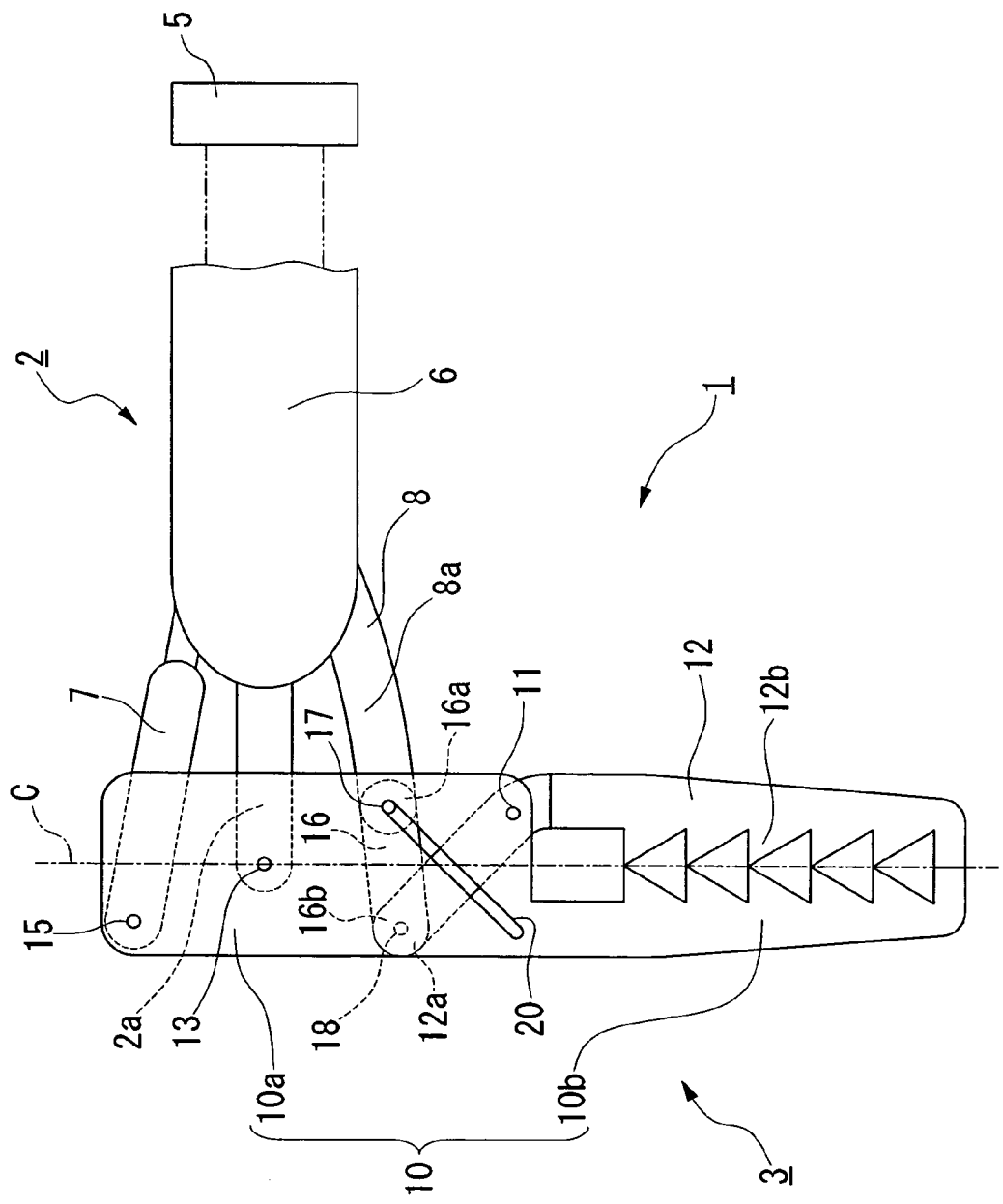
FIG. 3 is a side view of primary parts of the forceps for endoscope according to the embodiment of this invention in an oscillated state.

Subsequently, as shown in FIG. 3, an operation of oscillating to the second forceps member 12 side when the first forceps member 10 and the second forceps member 12 are closed will be explained.

Firstly, the oscillating operation axis member 7 is moved forward from the state shown in FIG. 1 to the forceps section 3 side. This force is transmitted as rotational momentum via the third pivotal supporting member 15 to the first forceps member 10, and the forceps section 3 begins to rotate counterclockwise (as seen in FIG. 1) around the second pivotal supporting member 13.

In accordance with this oscillation, the opening-closing operation axis member 8 is moved backwards.

When the third pivotal supporting member 15 is moved nearer the tip 2*a* side of the insertion section 2 than the second pivotal supporting member 13 in this way, the forceps section 3 rotates until the oscillating operation ends in the position shown in FIG. 3.

To return the forceps section 3 along the insertion section 2, the operation section 5 is manipulated to move the oscillating operation axis member 7 back to the operation section 5 side. This force is transmitted as rotational momentum via the third pivotal supporting member 15 to the first forceps member 10, and the forceps section 3 begins to rotate clockwise (as seen in FIG. 3) around the second pivotal supporting member 13.

By moving the third pivotal supporting member 15 nearer to the operation section 5 side than the second pivotal supporting member 13 in this way, the forceps section 3 is returned to its position in the direction following the insertion section 2.

Figure 4:
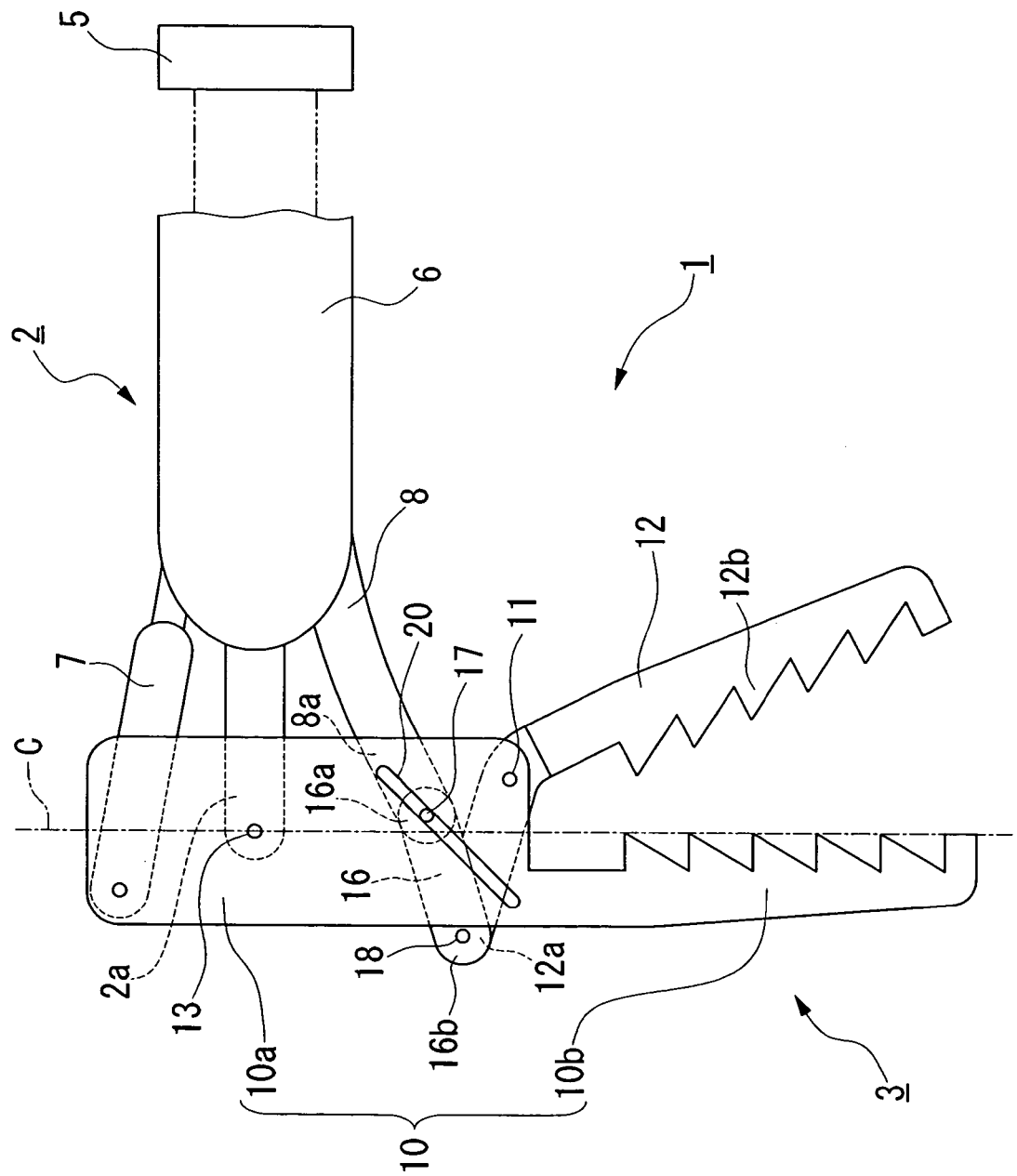
FIG. 4 is a side view of primary parts of the forceps for endoscope according to the embodiment of this invention when further opened in an oscillated state.

Subsequently, a method of further opening the forceps section 3 when it is in the oscillated state, as shown in FIG. 4, will be explained.

In the state shown in FIG. 3, the operation section 5 is manipulated to move the opening-closing operation axis member 8 forward in the same manner as already described. The tip 8a of the opening-closing operation axis member 8 now bends while moving the rotating axis member 17 along the leading groove 20.

When the opening-closing operation axis member 8 is moved further forward, the rotating axis member 17 moves along the leading groove 20 to the tip 10b side of the first forceps member 10, the fourth pivotal supporting member 18 is pushed to the outside of the first forceps member 10, and the base 12a of the second forceps member 12 is pushed to the outside via the fourth pivotal supporting member 18. Then, the second forceps member 12 rotates counterclockwise (as seen in FIG. 3) around the first pivotal supporting member 11.

In this way, the second forceps member 12 is opened to the operation section 5 side with respect to the first forceps member 10, as shown in FIG. 4.

To close the second forceps member 12 so that it is once again opposite the first forceps member 10, the operation section 5 is manipulated so that the opening-closing operation axis member 8 moves backward to the operation section 5 side. In a reverse movement to that described above, the rotating axis member 17 now moves along the leading groove 20 to the base 10a side of the first forceps member 10, whereby the fourth pivotal supporting member 18 returns to the operation section 5 side and the second forceps member 12 rotates clockwise (as seen in FIG. 4). Thus, the first forceps member 10 and the 12 are closed.

According to the forceps for endoscope 1, at the time of oscillating by rotating the forceps section 3 to the opening-closing operation axis member 8 side, the second pivotal supporting member 13 is able to rotate without interfering with the tip 8a of the opening-closing operation axis member 8, due to the fact that the tip 8a of the opening-closing operation axis member 8 is provided nearer to the tip 10a side of the first forceps member 10 than the second pivotal supporting member 13. Furthermore, since the second pivotal supporting member 13 and the third pivotal supporting member 15 are arranged in that sequence from the tip side 10a of the first forceps member 10 toward the base 10b side, rotation in the above-mentioned direction can be achieved without any interference between the second pivotal supporting member 13 and the oscillating operation axis member 7. Therefore, the forceps section 3 can rotate more than 90 degrees around the second pivotal supporting member 13.

On the other hand, when attempting to rotate the forceps section 3 to the oscillating operation axis member 7 side, the tip 8a of the opening-closing operation axis member 8 interferes with the second pivotal supporting member 13, and the tip 2a of the insertion section 2 interferes with the third pivotal supporting member 15; consequently, rotation in this direction can be restricted, minimizing the amount of protrusion of the connecting member 16 and the like from the forceps section 3 and reducing contact with the surrounding organism.

Since the leading groove 20, which the rotating axis member 17 clips into, extends from the base 10b side toward the tip 10a side of the first forceps member 10, and diagonally from the opening-closing operation axis member 8 side toward the fourth pivotal supporting member 18 side, at the time of opening and closing, the amount of movement of the tip 8a of the opening-closing operation axis member 8 is restricted to the position where it interferes with the second pivotal supporting member 13, enabling the amount of the connecting member 16 that protrudes outside the forceps for endoscope 1 to be reduced to a minimum.

This invention is not limited to the embodiment described above, and may be modified in various ways without deviating from its main points.

For example, although the leading groove 20 in the embodiment described above is a straight line, it may be curved instead.

Furthermore, although the tip 8a of the opening-closing operation axis member 8 is bendable in the description above, it may be made from stiff material if a new link member is added.

Since the forceps for endoscope of the present invention has the above constitution wherein the pivotal supports are positioned as described above, when oscillating the forceps section so that it rotates to the opening-closing operation axis member side, the tip of the opening-closing operation axis member and the second pivotal support can rotate without interference, due to the fact that the tip of the opening-closing operation axis member is nearer the tip side of the first forceps member than the second pivotal support. Furthermore, since the second and third pivotal supports are arranged in sequence from the tip of the first forceps member to the base thereof, the tip of the insertion section and the forceps section can rotate without interference. Thus, the forceps section can rotate more than 90 degrees around the second pivotal supporting member.

On the other hand, when rotating the forceps section to the oscillating operation axis member side, the tip of the opening-closing operation axis member interferes with the second pivotal supporting member, and the tip of the insertion section interferes with the third pivotal supporting member; whereby rotation in this direction can be restricted.

According to the forceps for endoscope of the present invention, the leading groove is formed in the first forceps member, thereby restricting the movement of the rotation axis member when opening and closing the forceps section. Further, since the leading groove extends from the base side of the first forceps member toward the tip side thereof, and diagonally from the opening-closing operation axis member side toward the fourth pivotal supporting member side, the forceps section can be opened and closed by moving the rotation axis member within the leading groove. Moreover, since the movement of the tip of the opening-closing operation axis member is restricted to the position where it interferes with the second pivotal supporting member, the amount of the connecting member that protrudes outside the forceps for endoscope can be reduced to a minimum.

What is claimed is:

1. A forceps for endoscope comprising:
an openable and closable forceps section, provided at the tip of an insertion section;
the insertion section having an oscillating operation axis member and a opening-closing operation axis member, which can move forward and backward in the axial direction;
the forceps section having a first forceps member and a second forceps member, the second forceps member being rotatable with a first pivotal support as a fulcrum and facing the first forceps member;
the first forceps member connecting to the insertion section so as to be rotatable around it with a second pivotal support as a fulcrum, and connecting to the oscillating operation axis member so as to be rotatable around it with a third pivotal support as a fulcrum;

the second pivotal support being arranged between the oscillating operation axis member and the opening-closing operation axis member;

the first pivotal support being arranged nearer the opening-closing operation axis member side than the second pivotal support;

a tip of the opening-closing operation axis member being provided nearer the tip side of the first forceps member than the second pivotal support; and the pivotal supports being arranged from a tip side of the first forceps member to a base side thereof in a sequence of first pivotal support, second pivotal support, third pivotal support.

2. The forceps for endoscope according to claim 1, further comprising a connecting member for connecting the second forceps member to the opening-closing operation axis member;

one end of the connecting section being connected to the opening-closing operation axis member so that it can rotate around it with a rotation axis member as a fulcrum;

another end of the connecting section being connected to a base of the second forceps member so that it can rotate around it with a fourth pivotal support as a fulcrum;

the fourth pivotal support being arranged on the opposite side of the rotation axis member with respect to the central axis of the forceps section;

the first forceps member having a leading groove, which the rotation axis member clips into; and the leading groove extending from the base side of the first forceps member toward the tip side thereof, and diagonally from the opening-closing operation axis member side toward the fourth pivotal support side.

* * * * *